United States Patent [19]

Siegmund et al.

[11] Patent Number: 5,630,784
[45] Date of Patent: May 20, 1997

[54] METHOD OF MAKING AND USING A RIGID ENDOSCOPE HAVING A MODIFIED HIGH REFRACTIVE INDEX TUNNEL ROD

[75] Inventors: Walter P. Siegmund, Pomfret Center, Conn.; Paul W. Remijan, Holland; John M. Smith, Southbridge, both of Mass.

[73] Assignee: Schott Fiber Optics Inc., Southbridge, Mass.

[21] Appl. No.: 467,965

[22] Filed: Jun. 6, 1995

Related U.S. Application Data

[62] Division of Ser. No. 992,660, Dec. 18, 1992, Pat. No. 5,423,312.

[51] Int. Cl.$^6$ .................................................. A61B 1/002
[52] U.S. Cl. .......................... 600/160; 600/920; 385/133; 385/902
[58] Field of Search ...................................... 600/160, 138, 600/920; 359/434, 435, 509, 810; 385/115–119, 128, 133, 902

[56] References Cited

U.S. PATENT DOCUMENTS

| | | |
|---|---|---|
| 2,843,112 | 7/1958 | Miller . |
| 3,257,902 | 6/1966 | Hopkins . |
| 3,261,349 | 7/1966 | Wallace . |
| 3,261,350 | 7/1966 | Wallace . |
| 3,261,351 | 7/1966 | Wallace . |
| 3,294,085 | 12/1966 | Wallace . |
| 3,297,022 | 1/1967 | Wallace . |
| 3,357,433 | 12/1967 | Fourestier et al. . |
| 3,832,029 | 8/1974 | Bryngdahl . |
| 4,168,882 | 9/1979 | Hopkins . |
| 4,215,678 | 8/1980 | Heine et al. . |
| 4,306,546 | 12/1981 | Heine et al. . |
| 4,364,629 | 12/1982 | Lang et al. . |
| 4,615,333 | 10/1986 | Taguchi . |
| 4,624,243 | 11/1986 | Lowery et al. . |
| 4,651,201 | 3/1987 | Schoolman . |
| 4,671,630 | 6/1987 | Takahashi . |
| 4,746,203 | 5/1988 | Nishioka et al. . |
| 4,760,307 | 7/1988 | Howorth . |
| 4,779,613 | 10/1988 | Hashiguchi . |
| 4,783,135 | 11/1988 | Utsumi et al. . |
| 4,784,118 | 11/1988 | Fantone et al. . |
| 4,802,460 | 2/1989 | Ohkawa et al. . |
| 4,850,342 | 7/1989 | Hashiguchi et al. . |
| 4,854,302 | 8/1989 | Allred, III . |
| 4,862,873 | 9/1989 | Yajima et al. . |

(List continued on next page.)

FOREIGN PATENT DOCUMENTS

| | | |
|---|---|---|
| 0019792 | 12/1980 | European Pat. Off. . |
| 0100517 | 2/1984 | European Pat. Off. . |
| 3818104 | 12/1988 | Germany . |
| 9014040 | 11/1990 | WIPO . |

*Primary Examiner*—Richard J. Apley
*Assistant Examiner*—John P. Leubecker
*Attorney, Agent, or Firm*—Millen, White, Zelano, & Branigan, P.C.

[57] ABSTRACT

The invention provides a rigid endoscope utilizing a high refractive index (HRI) tunnel rod, preferably made of glass, for transfer of image light from a distal end to a proximal end of the device, such HRI tunnel rod being modified so that a minimum of light is scattered and reflected within the rod, thus minimizing veiling glare and contrast reduction of the image which is formed near the HRI tunnel rod's proximal end. The HRI tunnel rod shortens the apparent distance from the proximal to the distal end by virtue of its refractive index being greater than that of air, and also provides a light tunnel which can carry the image over a relatively long distance by virtue of its modified inside walls. A preferred method of modification includes hydrogen firing of the HRI tunnel rod in order to create a thoroughly blackened inner surface which is highly non-reflective, even at grazing incidences. Relatively simple lenses are incorporated at the ends of the rod for image formation so as to cover a wide object field and to relay the image to a video camera. Stereo measuring embodiments of the endoscope provides dual optical paths for yielding two images containing parallax data.

10 Claims, 6 Drawing Sheets

U.S. PATENT DOCUMENTS

| | | |
|---|---|---|
| 4,947,245 | 8/1990 | Ogawa et al. . |
| 4,964,710 | 10/1990 | Leiner . |
| 4,979,498 | 12/1990 | Oneda et al. . |
| 4,988,172 | 1/1991 | Kanamori et al. . |
| 5,074,899 | 12/1991 | Howorth . |
| 5,078,773 | 1/1992 | Thomas . |
| 5,099,399 | 3/1992 | Miller et al. . |
| 5,179,620 | 1/1993 | Hosaka et al. . |
| 5,188,092 | 2/1993 | White . |
| 5,199,417 | 4/1993 | Muller et al. . |

METHOD OF MAKING AND USING A RIGID ENDOSCOPE HAVING A MODIFIED HIGH REFRACTIVE INDEX TUNNEL ROD

This is a division, of the application Ser. No. 07/992,660 filed Dec. 18, 1992, now patent No. 5,423,312

BACKGROUND OF THE INVENTION

The invention relates to rigid endoscopes for viewing into generally inaccessible areas, such as various body cavities or industrial components. Endoscopes for remotely viewing into body cavities or industrial components are well-known. Such endoscopes can be divided into two categories, rigid and flexible. Most flexible endoscopes utilize fiber optic image transfer bundles to carry the image from the distal tip to the proximal eyepiece. Other flexible endoscopes employ a small CCD chip at the distal tip and use fiber optics only for illumination and not for direct transfer of the image.

Most modern rigid endoscopes are of the "rod-lens" type, which utilize a train of rod-like lenses to relay the image of an object from a distal end to a proximal eyepiece or other viewing means, such as a CCD camera. Such a device is taught in U.S. Pat. No. 4,168,882 to Hopkins, whose entire disclosure is incorporated herein by reference. In that device, the image of an object area is formed by a first distal lens. A second lens reimages the first image to a third lens, which reimages the second image to a fourth lens, and so on, until the image is relayed to the viewing means.

Rigid endoscopes employing a train of lenses for image transfer require many lenses in order to transfer the image through a slender tube while retaining good resolving capabilities and a wide field of view. It is necessary that endoscope probe lengths reach as high as 30–40 centimeters, and such lengths require as many as 20–30 lenses in order to transmit a clear, bright image. Each lens requires grinding, polishing, and coating to obtain high optical quality, and must be aligned and mounted in a rigid encasement with great precision. As a result, the cost of producing such rigid endoscopes is very high. Further, such expensive rod-lens construction precludes the feasibility of removal and disposal of the whole shaft after a single use, which would be a preferred option, especially for cleanliness in medical applications. Removable, disposable sheaths which cover the length of the shaft have been proposed. However, such sheaths do not provide adequate protection against bacterial contamination, are cumbersome to work with, and are susceptible to breakage.

Stereo versions of rod-lens type endoscopes are also known in the prior art. For example, U.S. Pat. No. 5,122,650 to McKinley, the entire disclosure of which is incorporated herein by reference, teaches such an endoscope. However, substantial modifications to the basic rod-lens design must be made to obtain independent optical paths in the shaft portion in order to yield two images containing parallax data, such images being essential for production of a stereo image. These modifications require much duplication of optical elements, especially in the shaft portion, which results in an endoscope which is costly and is even less suitable for disposability of the shaft.

SUMMARY OF THE INVENTION

It is an object of the present invention to provide an improved rigid endoscope. This invention provides such an endoscope which can be constructed at a lower cost relative to prior art devices with comparable lengths and resolving capabilities. Moreover, the rigid endoscope of the invention comprises a shaft which is constructed in such a manner, and from such materials, as to allow it to be removed and disposed of at a low cost.

The present invention provides a rigid endoscope utilizing a solid transparent high refractive index (HRI) tunnel rod, preferably made of glass, in place of the conventional train of lenses discussed above, for conducting image light from a distal end to a proximal end of the device, the outer surface of such rod being modified so that a minimum of light is scattered and/or reflected within the rod, thus minimizing veiling glare and contrast reduction of the image which is formed by the proximal optics near the HRI tunnel rod's proximal end.

Relatively simple lenses are incorporated at the ends of the HRI tunnel rod for image formation so as to cover a wide object field and to relay the image to a receiving device, such as a video camera.

In one aspect, this invention provides a rigid endoscope device useful for remotely examining a cavity, comprising distal optics for forming an image of an object area to be examined, an HRI tunnel rod of transparent material having an index of refraction greater than 1 for conducting image light from a distal end to a proximal end of said endoscope, the HRI tunnel rod having an outer surface which is blackened effectively to inhibit internal scattering of light, proximal optics located at a proximal end of the HRI tunnel rod, the proximal optics serving to relay an image of an object area to be examined, and a means for receiving and displaying the image relayed from the proximal optics.

The HRI tunnel rod serves two major purposes: 1) it shortens the apparent distance from the proximal to the distal end by virtue of its refractive index being greater than that of air, and 2) it provides a light tunnel which can transmit image light over a relatively long distance without veiling energy from wall scatter by virtue of its modified inside walls. A preferred method of modification is by exposing the HRI tunnel rod to a reducing atmosphere, thereby reducing metal oxides to metal around the outer surface of the HRI tunnel rod to create a thoroughly blackened outer surface whose inner-diameter surface is greatly non-reflective, even at grazing incidences. A preferred reducing method is hydrogen firing, wherein the HRI tunnel rod is exposed to a heated atmosphere of hydrogen. Such methods are taught in detail in U.S. Pat. No. 4,760,307 to Howorth, U.S. Pat. No. 5,074,899 to Howorth, and U.S. Pat. No. 5,078,773 to Thomas.

In a second aspect, the invention provides an improved stereo measuring endoscope which resolves bright, clear images, contains fewer optical components, is less costly to manufacture, and which provides a shaft that may be disposed of at a low cost.

In a third aspect, the invention provides a method of producing a shaft for a rigid endoscope which is capable of accurately transmitting image light of high resolution from a distal end of the endoscope to a proximal end thereof, comprising modifying a rod of high refractive index transparent material by blackening the outer surface of the HRI tunnel rod, thereby creating an inner surface which minimizes the amount of light shattered and reflected within the HRI tunnel rod to an extent that veiling glare and contrast reduction of an image transmitted by the HRI tunnel rod are reduced, and surrounding the HRI tunnel rod with a ring of light-conducting members, the light-conducting members being oriented so as to run generally parallel to the HRI tunnel rod.

The foregoing and other objects, features, and advantages of the invention will be apparent from the following more particular description of the preferred embodiments as illustrated in the accompanying drawings in which reference characters refer to the same parts throughout the various views. The drawings are not necessarily to scale, emphasis instead being placed upon illustrating the principles of the invention.

Figure 1:
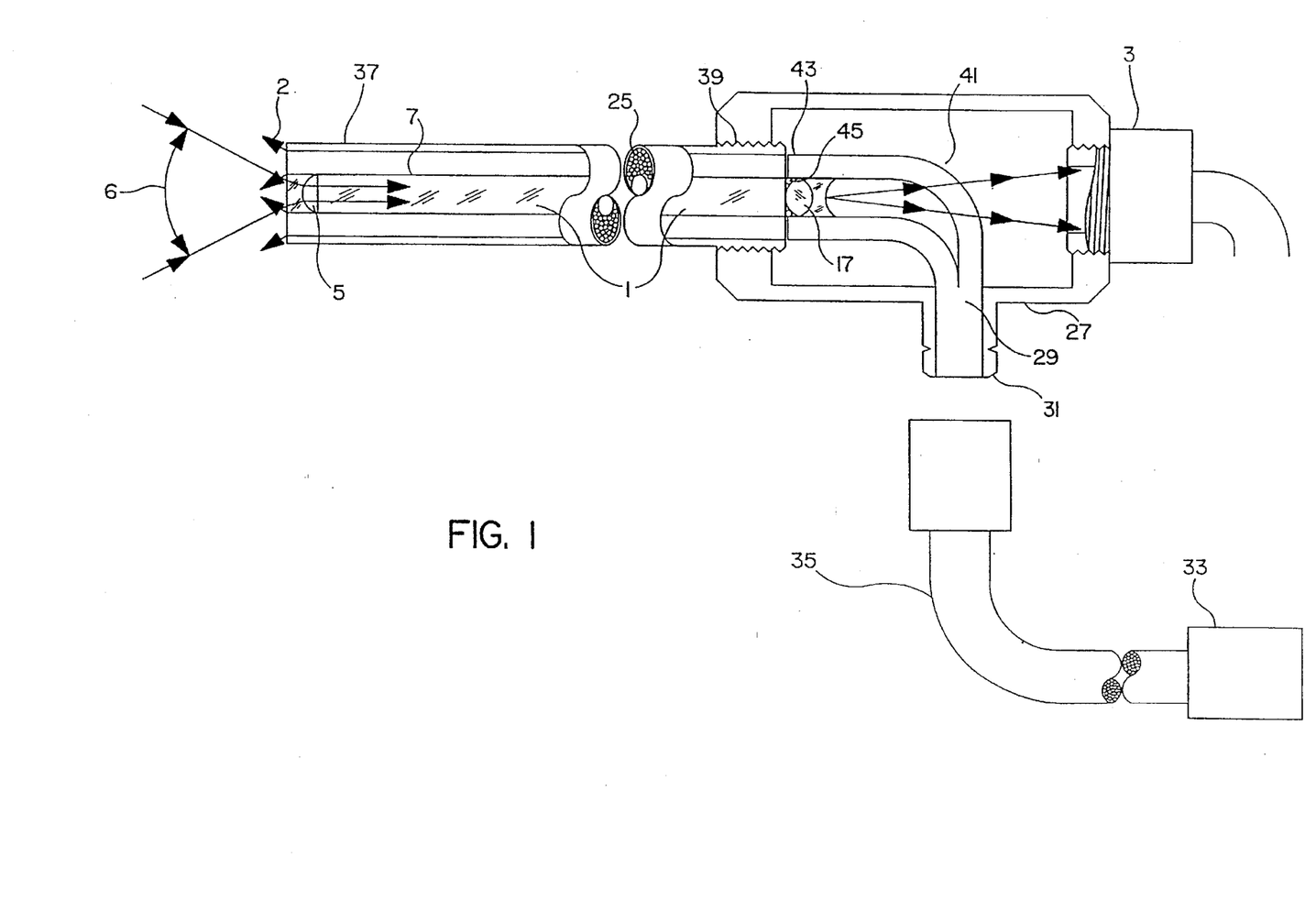
FIG. 1 shows the basic elements of the endoscope according to a preferred embodiment of the present invention.

As shown in FIG. 1, a solid transparent HRI tunnel rod 1 serves as an optical tunnel to allow the image formed by a relatively simple lens 5 at the distal end to be viewed by the eye, via an image-recording device 3, which may be a CCD camera or the like. In a preferred embodiment, the HRI tunnel rod 1 is made of glass; however, other transparent materials, including conventional polymers such as lucite, or even water, can be used for the rod's composition. The HRI tunnel rod shortens the apparent distance from the proximal to the distal end by virtue of its refractive index being greater than that of air.

If the walls of the HRI tunnel rod are modified in order to reduce internal light scattered or reflected from them, the resultant images are vastly improved over images obtained in the absence of such modification. Various methods may be used to accomplish this. A preferable method is by grinding, etching, sandblasting, or otherwise roughening the surface of the rod and then firing it at an elevated temperature in a reducing atmosphere, such as a hydrogen atmosphere. The hydrogen reduces certain metallic oxides present in the glass, such as lead or arsenic, to metal and causes the surface of the HRI tunnel rod to create a thoroughly blackened surface 7. The rod may be composed of a conventional high-index, lead-containing glass in order to aid in the hydrogen-firing process. Such a reducing treatment is disclosed in U.S. Pat. No. 5,078,773 to Thomas.

Another, less-effective method of modification is to grind, sandblast, or otherwise roughen the wall surface of the HRI tunnel rod and coat the so-treated surface with a black material, such as paint or resin, which preferably has a refractive index which closely matches that of the rod.

The distal optics 5, which may be either a positive or a negative lens or lens system, forms an image of the object space, generally a volume of low accessibility, that image being of generally reduced size. The object space may be, for example, the inside of an abdominal cavity. However, rigid endoscopes are also used for viewing the inside of industrial components such as weldments or castings.

The HRI tunnel rod 1, by virtue of its blackened surface and zero-focussing power, will "transfer" the image light along the endoscope shaft with minimal stray light interfering with the image. A relay lens 17 is provided at the proximal end of the HRI tunnel rod 1 to focus the image formed by the distal objective lens 5 onto the image-recording device 3. A rigid, elongated tubular housing 37 comprises a sheath made of stainless steel or glass, or other material.

A ring of optical fibers 25 is formed around the tunnel rod 1 to provide illuminating light 2 to illuminate the field of view 6. These fibers 25 terminate at the distal end of the shaft and have polished ends. The fibers 25 are routed in the handle 27 of the endoscope so as not to interfere with the optical path from the relay lens 17 to the imaging device 3, and are gathered together in a compact, generally circular bundle 29 and bonded into a tubular connector 31 mounted at the side or proximal end of the handle.

Light from a remote light source 33, which may be a Xenon arc lamp or other high intensity lamp, is transmitted to the connector 31 by means of a fiber optic cable 35. This cable may be separable or may be integral with the bundle 29.

A preferred embodiment of the endoscope has a separable shaft and handle to provide 1) disposability of the shaft, 2) interchangeable shafts of varying diameters or lengths, or 3) autoclavability of the shaft portion of the endoscope. In this embodiment, the shaft may consist of a glass HRI tunnel rod and a surrounding ring of light-conducting material, fibers or clad rods. A surrounding housing such as a stainless steel or glass tube may be provided, or the light-conducting material may serve also as a housing. For example, an aluminum-coated plastic tube may serve as both the housing and light-guide illuminator.

A simple mechanical coupling 39, FIG. 1, may be used to lock the shaft into the handle. Such coupling may be a ball detent, collet, threaded locking ring, or other means.

The handle may contain the relay lens placed just behind the proximal end of the HRI tunnel rod 1, and may also contain a fiber bundle resembling a "cobra head" to form a ring of fibers 41 to optically couple to those in the shaft in very near contact (or actual contact) at a coupling point 43. A suitable light-tight ring seal 45 is used to prevent any of the light carried by the fibers 41 from entering the optical path of the image light in the space between the HRI tunnel rod 1 and the relay lens 17.

Whereas the handle 27 may not be steam sterilizable, it may be gas sterilized in ethylene oxide gas or disinfected and/or sterilized by other appropriate means. The housing 37 may be made from metals or plastic or combinations thereof.

Figure 2:
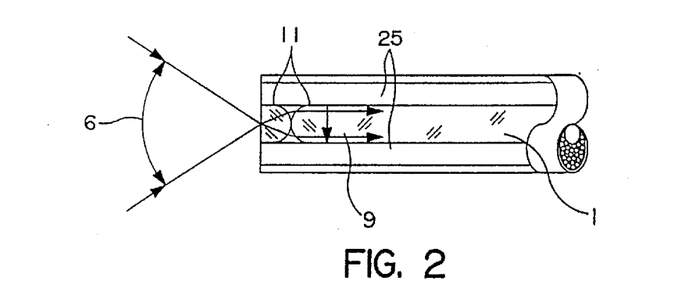
FIG. 2 shows an embodiment of the present invention wherein a positive lens is used as the distal optics.

As shown in FIG. 2, if a positive objective lens 11 is used as the distal optics, a real image 9 is formed at or near the entrance face of the HRI tunnel rod 1.

Figure 3:
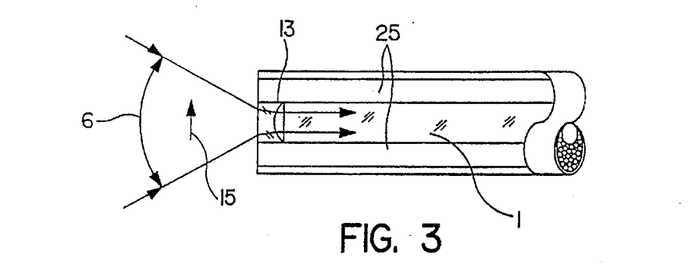
FIG. 3 shows an embodiment of the present invention wherein a negative lens is used as the distal optics.

As shown in FIG. 3, if a negative objective lens 13 is used, a virtual image 15 is formed in front of the negative lens 13. The distal and proximal optics in each of the embodiments may be simple plano-convex or plano-concave lenses, combinations of simple lenses, or more complex structures with aspheric surfaces for correction of image aberrations.

Figure 4:
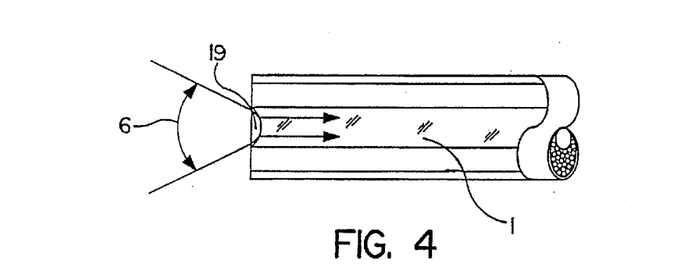
FIG. 4 shows an embodiment of the present invention wherein a concave "dimple" is formed on the distal end of the HRI tunnel rod.

As shown in FIG. 4, a simple form of objective lens may be utilized by incorporating a concave "dimple" 19 into the distal end of the HRI tunnel rod 1. The dimple 19 may be formed by grinding and polishing a concave surface directly into the end of the solid glass HRI tunnel rod 1, or such may be accomplished by hot-pressing the end of the rod.

Figure 5:
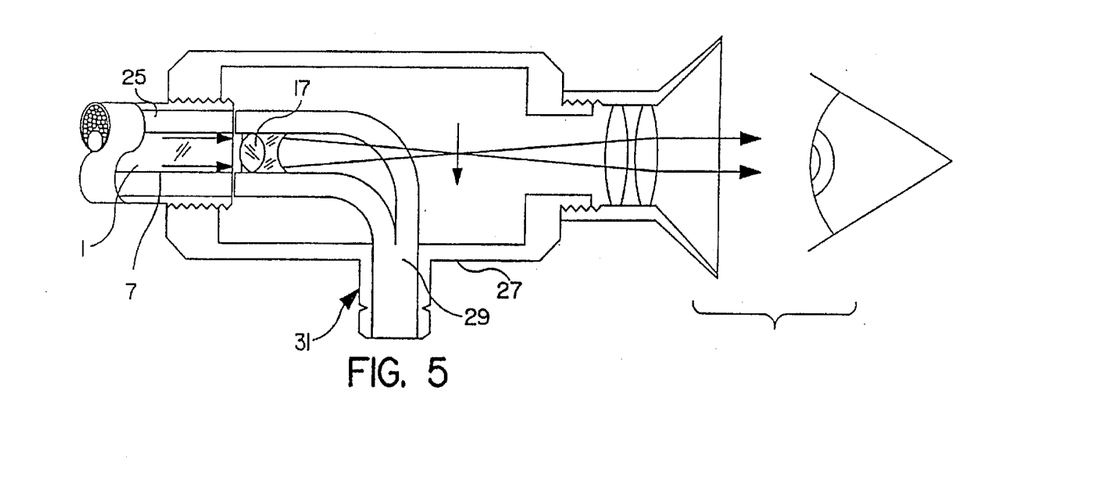
FIG. 5 shows an embodiment of the present invention wherein an eyepiece is used as a means of viewing the image produced.

As shown in FIG. 5, the real image produced by relay lens 17 can be viewed directly through an eyepiece 21. In this case, if a negative objective lens is used, a means for erecting the image is required. An aperture 23 placed between the relay lens 17 and the HRI tunnel rod 1 can be used to cut off rays which travel very close to the inner-diameter of the blackened surface 7 of HRI tunnel rod 1 and which may-be distorted due to any slight inhomogeneities in the rod near these walls.

The entire shaft, including the HRI tunnel rod 1 and fibers 25, may be made of low cost materials, and hence be disposable after one use or after limited use. In one such embodiment, shown in FIG. 6a and 6b, the shaft is made of an all-glass construction with a pre-blackened HRI tunnel rod 1 surrounded by glass-clad fibers 51a or keystone-shaped rods 51b, and surrounded by a glass housing 53 having a low coefficient of thermal expansion. This provides a mechanically very rugged construction for the shaft. Although both glass-clad fibers 51a and keystone-shaped rods 51b appear in FIG. 6a for purposes of illustration, an embodiment using a single light-conducting material may be preferable for purposes of design-simplification.

Figures 6A, 6B:
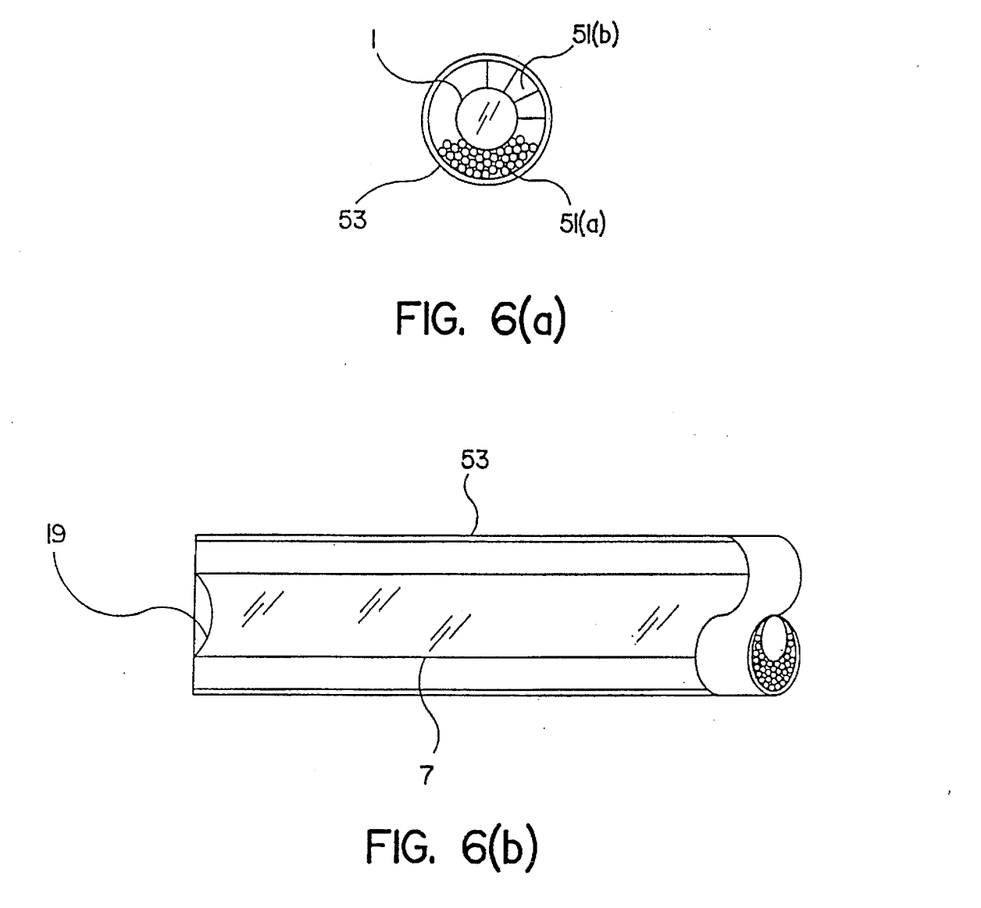
FIG. 6a and 6b show an embodiment of the present invention wherein the shaft is of an all-glass, integral construction.

The outer glass housing 53 may also be blackened, such as by firing in hydrogen, to produce a glossy black finish. Such an integral shaft may be made by assembling the pre-drawn and blackened glass rod along with a ring of light pipes into the glass housing and redrawing at a relatively low drawing ratio (such as 2:1) to thermally fuse all the glass elements into a sealed, void-free rod.

To reduce internal reflection or scattering of light in this version, the surface of the HRI tunnel rod, which is oversized in diameter prior to the final draw to the desired diameter, may be modified by very coarse grinding and/or cutting of shallow, circular, or spiral grooves (by sandblasting through a mask, for example) so as to produce shallow baffles inside the HRI tunnel rod. The rod may then be fired in a reducing atmosphere to blacken the roughened and grooved exterior surface. This also causes the interior "surface" of the rod to appear very black.

When this rod is assembled with the light piping clad rods in a glass tube and redrawn, there will be some smoothing and flattening of the rough surface and the grooves, but the remaining roughness and modified grooved surface will still adequately serve to suppress the internal reflection and scattering of the HRI tunnel rod after final drawing.

Figure 7:
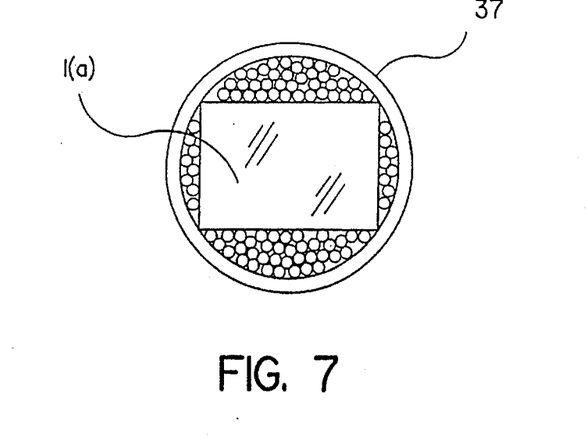
FIG. 7 shows an embodiment of the present invention wherein the shaft of the device is rectangular in cross-section.

In the embodiments shown in FIGS. 1-6, the housing and HRI tunnel rod are formed so as to be circular in cross-section. However, as shown in FIG. 7, it is also foreseeable that an HRI tunnel rod 1a which is rectangular in cross-section could be used. Such an embodiment might be advantageous in order to conform the shape of the image output to the shape of the detector used. For example, CCD detectors are generally available in rectangular form, and thus an endoscope which uses such a detector would benefit from a rod and housing which produce a rectangular image.

Figure 8A:
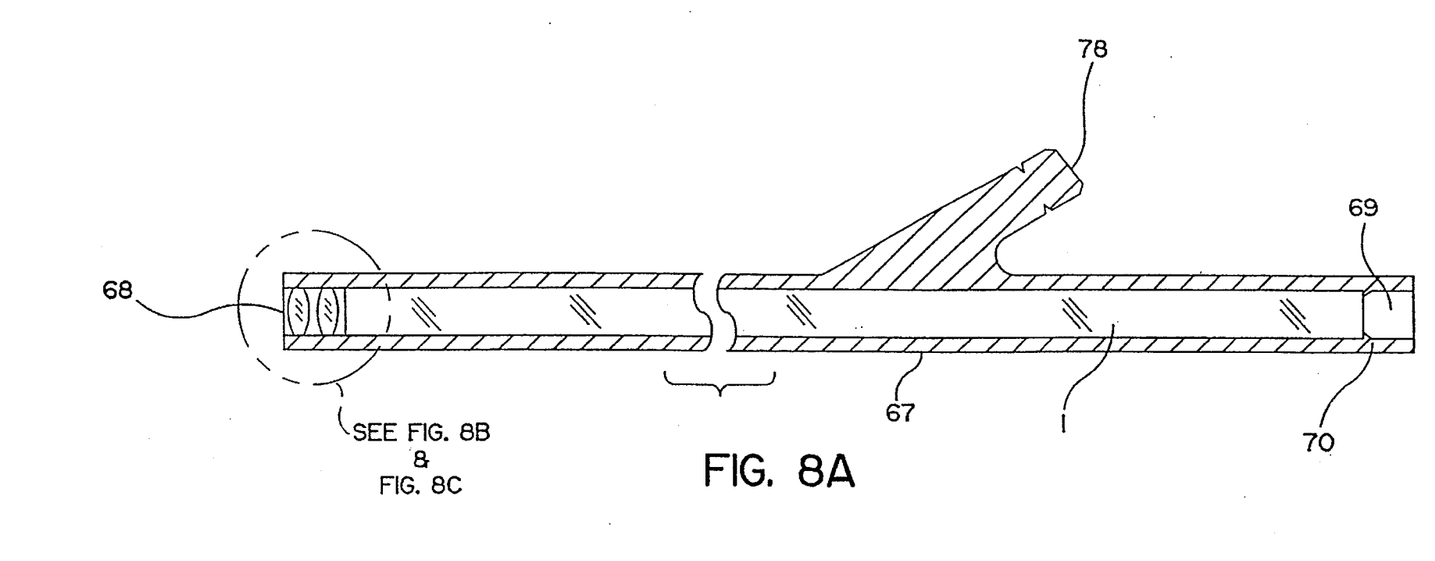
FIG. 8 shows an embodiment of the present invention wherein the tunnel tunnel rod is surrounded by a solid light-conducting sleeve.
Figure 8B:
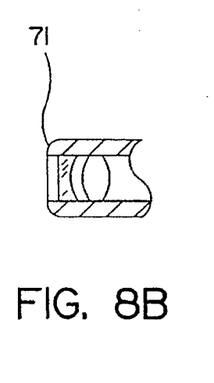
Figure 8C:
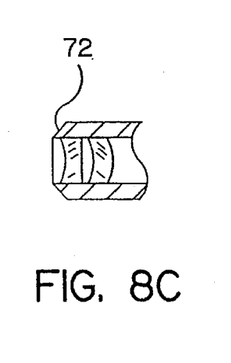

FIG. 8 illustrates an embodiment wherein a light-conducting sleeve 67 provides a cavity for transfer of illumination energy to the object. A typical illumination input point is shown at 78. Use of a plastic light-conducting sleeve is compatible with the concept of ultrasonically or chemically welding plastic distal optics 68 into the distal tip. The shaft depicted in FIG. 8 is completed by inserting the HRI tunnel rod 1 via the opening at the proximal end 69. Flexible tabs 70 at the proximal end of the light-conducting sleeve could be used to retain the HRI tunnel rod. Examples of distal end configurations 71 and 72, providing different illumination fields, are also shown.

Figure 9:
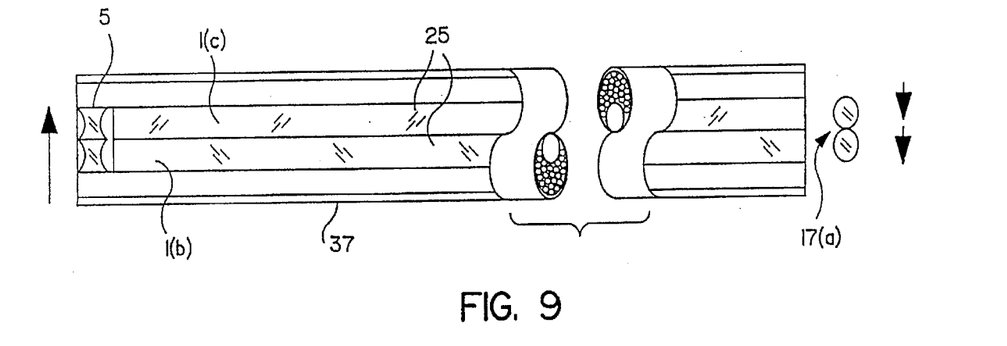
FIG. 9 shows an embodiment wherein there is provided a twin-channel light shaft which produces a stereo image pair from a single object.
Figure 9A:
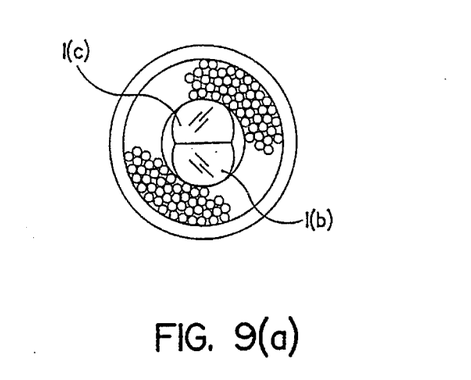
FIG. 9a shows a cross-section of the shaft shown in the embodiment of FIG. 9.
Figure 10:
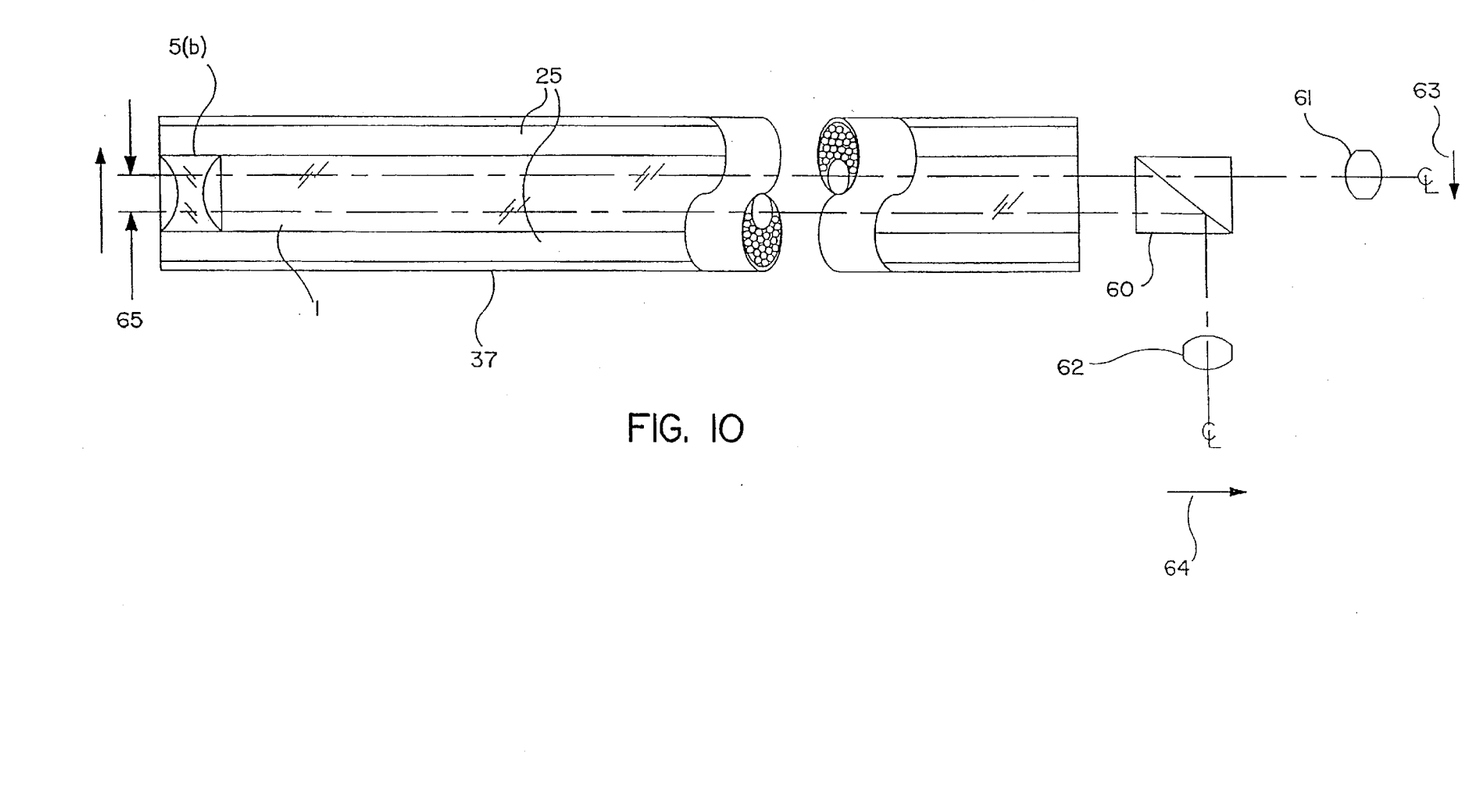
FIG. 10 shows an embodiment wherein there is provided an arrangement of relay optics which produces a stereo image pair from light transferred by a single HRI tunnel rod and single set of distal optics.

FIGS. 9 and 10 show configurations which generate "stereo images", such images being the source of parallax data which reveals the object distance from the distal tip. In FIG. 9, the "stereo images" are generated by duplicating the basic optical system of FIG. 1 within a single shaft. This embodiment comprises dual distal optics 5a and dual proximal optics 17a, and dual HRI tunnel rods 1b and 1c. In FIG. 10, the shaft contains one set of distal optics 5b and one HRI tunnel rod 1. Two sets of relay optics 61, 62 interact with and are coupled to the shaft optics via beam splitter 60 to form images 63 and 64. With properly-designed relay optics, the stereo base 65 in the embodiment of FIG. 10 can approach or even exceed the HRI tunnel rod's diameter. The ability to increase the stereo base beyond the HRI tunnel rod's diameter provides an increased depth resolution.

While the invention has been particularly described with reference to preferred embodiments thereof, it will be understood by those skilled in the art that various changes in form and details may be made therein without departing from the spirit and scope of the invention.

The embodiments of the invention in which an exclusive property or privilege is claimed are defined as follows:

1. A method of producing an endoscope shaft which is capable of accurately transmitting image light from a distal end of an endoscope to a proximal end thereof, comprising:
   modifying a rod of transparent material, said material having an index of refraction greater than one and having substantially zero focussing power, by blackening an outer surface of said rod, thereby creating an inner surface which minimizes the amount of light scattered and reflected within said rod to an extent that veiling glare and contrast reduction of an image transmitted by said rod are reduced.

2. The method of claim 1, further comprising the step of: roughening the surface of said rod prior to said blackening step.

3. The method according to claim 1, wherein said modifying step includes a step of firing said rod in a reducing atmosphere.

4. The method according to claim 3, wherein said reducing atmosphere is hydrogen.

5. The method according to claim 1, wherein the degree of said blackening is equivalent to that achieved by firing said rod in a reducing atmosphere.

6. The method according to claim 1, wherein the degree of said blackening is such that grazing rays are not substantially reflected within said rod.

7. The method of claim 1, further comprising the step of: surrounding said rod with a ring of light-conducting members, said light-conducting members being oriented so as to run generally parallel to said rod.

8. The method according to claim 7, further comprising: fusing said rod and said light-conducting members so as to form a single, integral shaft component.

9. A method of examining a cavity, comprising:
   providing a tunnel rod of transparent material having an index of refraction greater than one, substantially zero focussing power, and an outer surface which is blackened effectively to inhibit internal scattering of light;

inserting said tunnel rod into said cavity; and viewing said cavity via said tunnel rod.

10. The method according to claim 9, wherein said cavity comprises a portion of the human body.

* * * * *